United States Patent [19]

Maitland

[11] 4,166,533
[45] Sep. 4, 1979

[54] BIOSTABLE SELF-CONTAINED PACKAGE OF A PLURALITY OF VETERINARIAN SYRINGES

[75] Inventor: Robert L. Maitland, Norwich, Conn.

[73] Assignee: Masti-Kure Products Company, Inc., Norwich, Conn.

[21] Appl. No.: 875,852

[22] Filed: Feb. 7, 1978

[51] Int. Cl.² ............................................. B65D 77/22
[52] U.S. Cl. .............................. 206/366; 206/45.14; 206/383; 206/485
[58] Field of Search ............... 206/366, 365, 382, 383, 206/379, 371, 443, 485, 214, 45.12, 45.14, 45.31, 45.33, 45.34

[56] References Cited

U.S. PATENT DOCUMENTS

| | | | |
|---|---|---|---|
| 689,667 | 12/1901 | Blakeslee | 206/485 |
| 1,021,998 | 4/1912 | Myers | 206/443 |
| 1,176,932 | 3/1916 | Smith | 206/45.14 |
| 1,838,411 | 12/1931 | Knorpp | 206/45.14 |
| 1,896,677 | 2/1933 | Myers | 206/45.14 |
| 3,133,635 | 5/1964 | Gardon | 206/366 |
| 3,207,302 | 9/1965 | Hobbs | 206/366 |
| 3,305,084 | 2/1967 | Higgins | 206/366 |
| 3,746,155 | 7/1973 | Seeley | 206/365 |
| 3,904,029 | 9/1975 | Kaltz | 206/44.12 |
| 3,918,583 | 11/1975 | Adams | 206/45.14 |

*Primary Examiner*—Herbert F. Ross
*Attorney, Agent, or Firm*—Murray and Whisenhunt

[57] ABSTRACT

There is provided a biostable package of syringes of the type having a barrel, piston and nozzle. The package comprises a self-supporting syringe holder having an enclosure means with upper, lower, side and end walls for receiving a portion of a syringe such that at least the nozzle thereof is disposed within the enclosure means. Circular sealing apertures are disposed in the upper wall of the enclosure means for receiving the syringes and bendable sealing flaps are disposed around the periphery of each sealing aperture to form a non-dust seal around the syringe. An upstanding panel projects from the enclosure means and a rupturable plastic film extends from the walls of the enclosure means to the upstanding panel whereby the syringes are biostably sealed from ambient contamination. When the film is removed the portion of the syringe disposed in the enclosure means is non-dust sealed from solid contamination.

10 Claims, 6 Drawing Figures

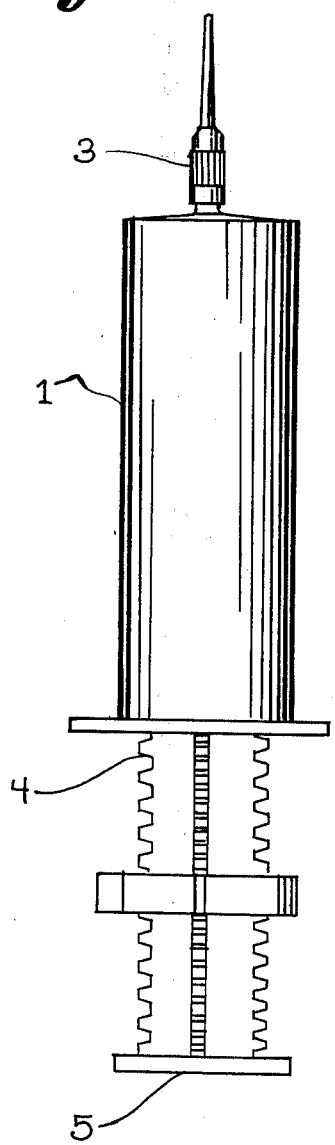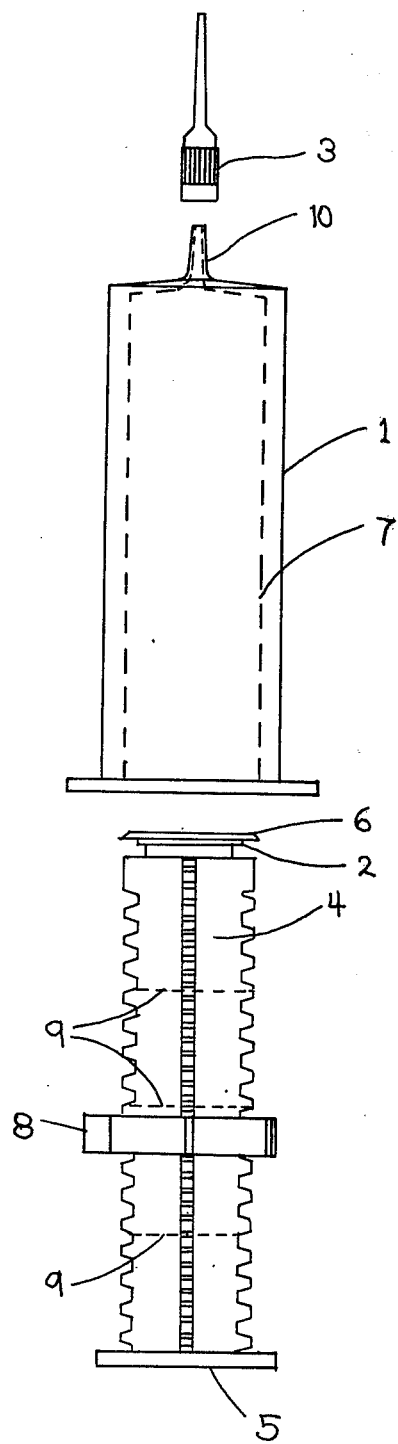
Fig. 1
Fig. 2

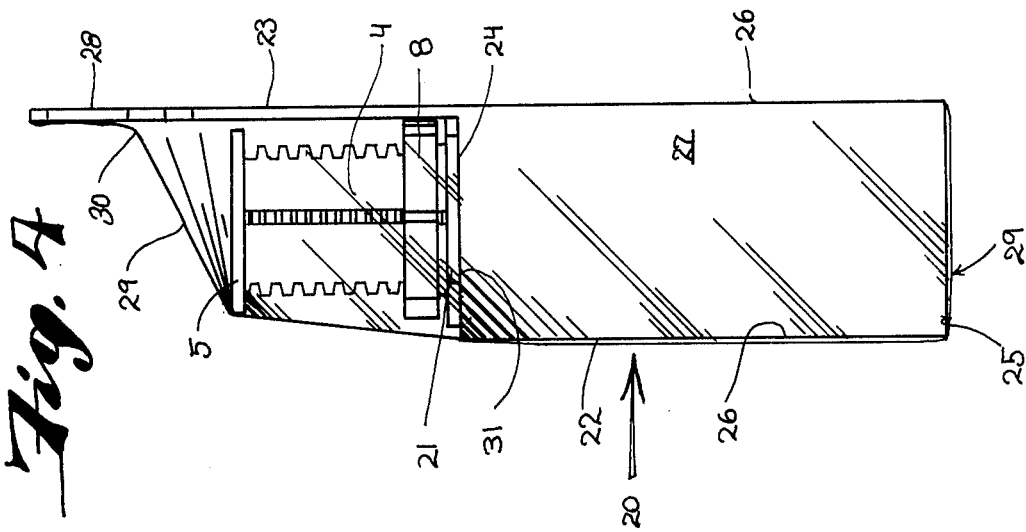
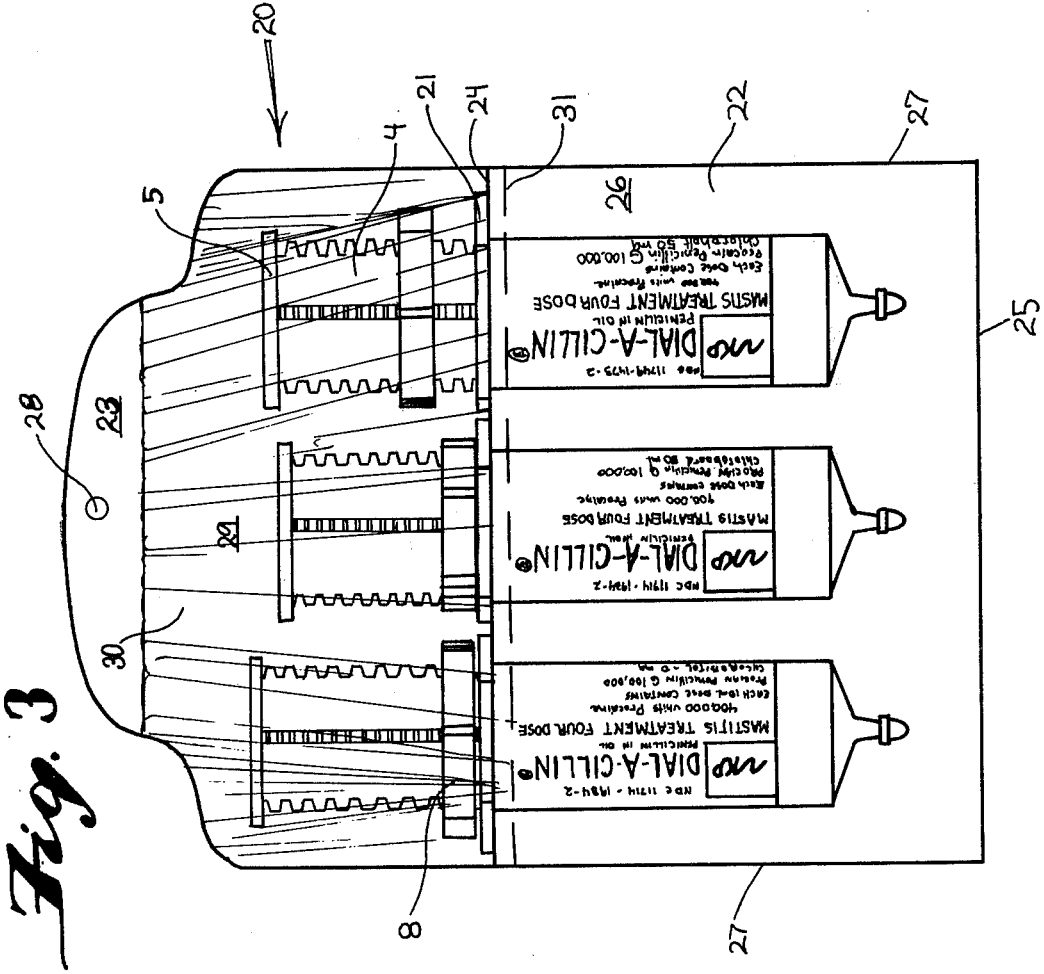

BIOSTABLE SELF-CONTAINED PACKAGE OF A PLURALITY OF VETERINARIAN SYRINGES

The present invention relates to a biostable, self-contained package of a plurality of veterinarian syringes of the type having a cylindrical barrel, piston therein and discharge nozzle, wherein the syringes are biostably sealed in the package, but once the package is ruptured for removal of the syringes, at least the nozzle of the syringes remains sealed from solid non-dust contamination.

BACKGROUND OF THE INVENTION

Contamination of veterinarian syringes designed for field use is a constant problem in the art, since such use is in environments where sources and opportunities for contamination are great. For example, in the dairy industry, mastitis in dairy cows is a constant problem and a conventional means of combating that problem is the injecting of a microbicide into the teats of the cows. This injection takes place in the dairy barn, which contains many sources and opportunities for contamination of the syringe used for the injection. That contamination may carry other bacteria and the use of such contaminated syringe may induce other unwanted conditions and diseases in the cows.

While many means of avoiding such contaminations are known, including protective devices such as containers, boxes, bags, and the like, these devices are not normally economical, since they entail considerable expense in both the protective devices themselves and the labor required to use those protective devices. For example, when a large number of cows must be inoculated, the opening and closing of protective devices is too time consuming.

Alternatively, a syringe may contain only the required injection for one teat, hence allowing disposing of that syringe to avoid contamination, but this is quite expensive in that cost of the syringes, per se. For this reason, multiple dose syringes, i.e., syringes containing at least four doses, are normally used.

It is to the multiple dose syringes that the present invention has particular relevancy. These syringes are of the type which have a cylindrical barrel, a piston movable in the barrel to discharge a measured dose of the contents and a discharge nozzle for dispensing the contents. The discharge nozzle is normally of the type which is detachable and disposable, since usually only one quarter of a lactating cow will be infected and since the nozzle used to inject one teat could contaminate another teat of the same or other cow which does not have mastitis.

Heretofore, these multiple dose syringes have been individually packaged. This is not only expensive but when the package is ruptured the syringe may be contaminated by the dairy barn environment. Alternatively, a plurality of these syringes have been contained in a single package to decrease the packaging cost per syringe, but here again, once the package is ruptured, all of the syringes may be contaminated by the dairy barn environment. As noted above, any protection against such contamination must be relatively inexpensive and the use thereof must not materially increase the time for injection of the cows, or otherwise that protection becomes prohibitively expensive, especially in view of the relatively small profit margin of the dairy farming industry.

Accordingly, it would be of significant advantage in the art to provide relatively inexpensive packages for multiple dose syringes which do not materially increase the cost of the packaged syringes and which do not materially increase the labor required for use of those syringes.

BRIEF SUMMARY OF THE INVENTION

There is provided a biostable, self-contained package of a plurality of multiple dose veterinarian syringes of the type having a cylindrical barrel, piston therein (along with an associated plunger) and disposable discharge nozzle. The package comprises a self-support and free-standing syringe holder including an enclosure means having upper, lower, side and end walls for receiving and enclosing a portion of the syringe such that at least the discharge nozzle thereof is disposed within the enclosure means. A plurality of circular sealing apertures are disposed in the upper wall of the enclosure means for receiving the syringes into the enclosure means. A plurality of angular shaped bendable sealing flaps are disposed around the periphery of each of the sealing apertures and the flaps extended radially into the sealing aperture so that when the sealing flaps lie in the plane of the upper wall the sealing aperture is essentially closed. But when the sealing aperture has a syringe received therein, the sealing flaps are bent into the enclosure means and form a close non-dust seal around the syringe. A plurality of syringes are received by the sealing apertures and partially disposed in and, thus enclosed by the enclosure means, with the plunger thereof oriented upwardly in the vertical direction. An upstanding panel projects from the enclosure means and extends vertically beyond the syringe plunger. A rupturable impervious plastic film extends from the end walls and at least one side wall of the enclosure means to a portion of the upstanding panel which is vertically beyond the plunger. By this arrangement, the enclosure means and the syringes are biostably sealed from ambient conditions by the rupturable film. Even when the rupturable film is removed, the portion of the syringes disposed in the enclosure means is non-dust sealed from solid contamination.

In this latter regard, it is to be understood that the term "non-dust sealed" means that the protection is not effective against air carried dust but is effective toward solid contamination of particle sizes greater than dust, i.e., particle size which are not inherently air dispersed. Such particle size, therefore, include hay fines, straw particles, dirt, and the like, all of which are at various times displaced from a resting position in ordinary dairy barn operations. On the other hand, the term "biostably sealed" is intended to mean that microbial contamination within the package does not increase by virtue of ambient contamination within the field use, i.e., the dairy barn. This is, of course, by virtue of the impervious plastic film sealing the enclosure and syringes until the time that the impervious plastic film is ruptured for removal of a syringe.

BRIEF DESCRIPTION OF THE DRAWINGS

FIG. 1 shows a syringe of the type to which the present invention relates.

FIG. 2 shows the syringe of FIG. 1 in an exploded view.

FIG. 3 shows a front view of an embodiment of the invention where the syringes of FIG. 1 are partially contained within the enclosure means.

FIG. 4 is a side view of FIG. 3.

DETAILED DESCRIPTION OF THE INVENTION

Figure 5:
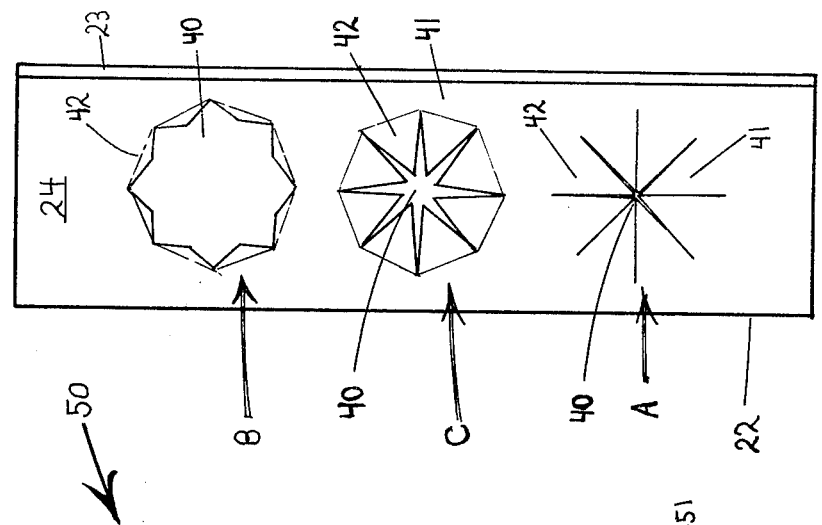
FIG. 5 is a top view of FIG. 3 without the syringes.

As shown in FIGS. 1 and 2, the syringes to which the present invention has particular relevance are of the type having a cylindrical barrel 1, piston 2 therein, and a discharge nozzle 3. As is typical with these syringes, the piston has a plunger 4 with a top plate 5 for applying pressure to the piston, e.g., with the thumb of the user on top plate 5 (a flange as shown in the drawing may be provided for holding the syringe between the index and second fingers).

As better seen in FIG. 2, the piston 2 has a skirt 6 which forms a seal between the piston and inside surface 7 of barrel 1. Plunger 4 is threaded to allow dosage adjustment ring 8 to be threadedly moved upwardly and downwardly on the plunger. Thus, the stroke of piston 2 can be varied whereby the amount of contents contained in cylindrical barrel 1, which is discharged, can be varied according to the position of ring 8. Normally, four dosage marks will be made on the plunger, as indicated at 9, so that four doses may be expelled from the same syringe.

For the reasons explained above, it is preferable that nozzle 3 be detachable from orifice projection 10 so that once the nozzle has been used in injecting a first dose from the syringe, that nozzle may be discarded. Protective cap 11 is then placed on projection 10 until the syringe is to again be used. At that time, protective cap 11 is removed and a new nozzle 3 is placed thereon for a second injection from the syringe. If desired, both nozzle 3 and protective cap 11 may be disposable and are conveniently pre-packaged in sterilized blister packs, shrink packs, or the like. A sufficient number of nozzles (and preferably protective caps) for all doses of all syringes are packaged in the syringe packaging.

Turning now to FIGS. 3, 4 and 5, it will be seen that the invention provides a self-supporting and free-standing syringe holder 20 containing a plurality of syringes of the type having a cylindrical barrel, piston therein and discharge nozzle. (See FIG. 1) The holder 20 has an enclosure means 22. The holder also includes an upstanding panel 23 which projects from the enclosure means and extends vertically beyond the syringe plunger. The enclosure means has an upper wall 24, a lower wall 25, side walls 26, and end walls 27. In the preferred embodiment shown in FIGS. 3 through 5, the enclosure means 22 is of sufficient depth to receive essentially all of the barrel of the syringe, although this is not critical, as will be discussed more fully hereinafter in connection with FIG. 6. However, for this preferred embodiment, since the barrel of the syringe is preferably contained totally within the enclosure means 22, and since the enclosure means may not have a transparent front side wall 26, the labeling on the syringes can not be read when the syringes are in place. To this end, labeling which is essentially the same as on the barrel of the syringe may be placed on the opaque front side wall 26 so that the contents of the syringe may be identified by the user. Alternatively, of course, front side wall 26 could be a transparent material so that the labeling on the syringes is observable by the user.

It will be observed from these Figures that the syringe holder 20 is a self-supporting and free-standing syringe holder. Thus, the syringe holder may simply be placed on a flat surface and will be free-standing or self-supporting depending upon the orientation of the holder on the flat surface. It is therefore convenient to place the holder on a shelf, in a cabinet, or the like. Alternatively, the upstanding panel 23 may have a hanging aperture 28 from which the package may be suspended. It will also be noted in connection with FIGS. 3 and 4 that the package also has provided a rupturable impervious plastic film 29 (shown as a transparent film) extending from the end walls 27 and at least one side wall 26 of the enclosure means to a portion of the upstanding panel 23 which is vertically beyond plunger 4. Also, as shown in that drawing, hanging aperture 28 is vertically above the juncture 30 of plastic film 29 and upstanding panel 23, whereby the hanging aperture is not within the rupturable film and the package may, accordingly, be hung by hanging aperture 28 without rupturing film 29.

Turning now to the details of the enclosure means, it will be seen that the enclosure means is configured for receiving and enclosing a portion of syringe 1 such that at least the nozzle 3 thereof is disposed within the enclosure means. As shown in FIGS. 3 and 4, actually, essentially the entire barrel and nozzle of the syringe are disposed within the enclosure means, although this is not required, as will be shown in more detail in connection with FIG. 6.

As best seen in FIG. 5, upper wall 24 of enclosure means 22 has a plurality of circular sealing apertures 40 for receiving syringes 1 into the enclosure means. As can be best seen from FIGS. 3 and 4, a plurality of syringes 1 are received by the sealing apertures 40 and partially disposed in and enclosed by enclosure means 22, with the plunger 4 of the syringes oriented upwardly in the vertical direction.

Disposed around the periphery 41 of each sealing aperture 40 is a plurality of angularly shaped, bendable sealing flaps 42. These sealing flaps 42 extend radially into the sealing aperture so that when the sealing flaps lie in the plane of the upper wall 24, the sealing aperture is essentially closed, as shown in sealing aperture A of FIG. 5. But when the sealing aperture has a syringe received therein, the sealing flaps 42 are bent into the enclosure means 22 and will form a close non-dust seal around the syringe, as shown in FIG. 5 by sealing aperture B. For illustration purposes, sealing aperture C shows sealing flaps 42 in a partially bent configuration (extending into the enclosure means 22). While somewhat exaggerated, the configuration of sealing flaps 42 in sealing aperture C illustrates the configuration of those flaps when a syringe has been withdrawn from sealing aperture C, especially when the enclosure means or at least the sealing flaps are made of a relatively resilient material, such as a resilient polymer coated paper, resilient plastic and the like. It will be appreciated, therefore, that upon reinsertion of the syringe into the enclosure means the non-dust seal will be reestablished.

It will also be specifically appreciated that the arrangement of the sealing aperture provides very substantial advantages. First of all, the aperture may be made by a simple punch/scoring operation onto a flat wall of the enclosure means. This is an exceedingly inexpensive means of making a non-dust sealing aperture and provides economies for the package, which make the package quite attractive for field use, such as in dairy barns, for the reasons explained above. While other sealing apertures have been disclosed in the prior art, even sealing apertures with more effectiveness, these known sealing apertures do not enjoy the substantial economic advantage of manufacture of the present sealing aperture and are, accordingly, not satisfactory for the purpose of the present invention. Further, the present sealing apertures are sufficiently effective for non-dust sealing application that substantial contamination of the syringe ends or tips is avoided.

With the present arrangement, the enclosure means and the syringes are biostably sealed from ambient contamination by the rupturable film. A plurality of these packages, therefore, may be advantageously placed about a dairy barn for easy use and reach in injecting cows. When it is desired to inject cows, the package will contain enough syringes, i.e., three to twelve syringes, so that the worker may quickly obtain a syringe, inject cows and obtain additional syringes without great loss of time in obtaining additional syringes from a supply thereof distant from the place where the cows are being injected.

Even after the rupturable film has been removed, the portion of the syringe disposed in the enclosure means is non-dust seal from solid contamination. Therefore, even with substantial movement of livestock, people, and machinery through dairy barns and the attendant dispersement of solid contamination in the air (non-dust contamination), that portion of the syringe contained in the enclosure means will be protected. Hence, bits of straw, mud, dirt, feed, hay, and the like, which are commonly dispersed in the air by virtue of movement of men, machinery, and animals will not lodge next to or onto the portion of the syringe in the enclosure means. Since it is only necessary that the nozzle be protected from this contamination, i.e., it is the only portion which actually enters the teats of a cow, it is only necessary that the nozzle be within the enclosure means. Although, for an added measure of protection, it is preferred that the entire barrel of the syringe be within the enclosure means, as shown in FIGS. 3 and 4.

Figure 6:
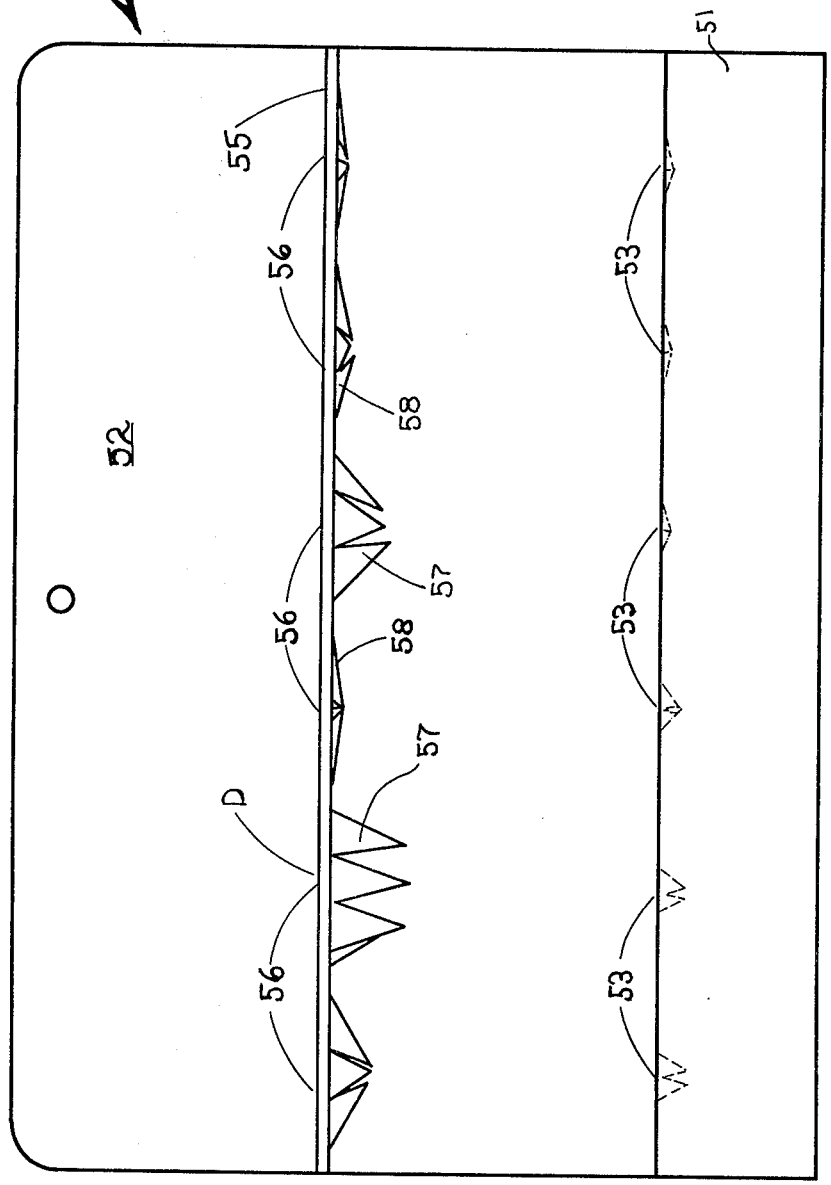
FIG. 6 is a front view of another embodiment of the enclosure means of the invention, without the syringes.

However, if desired, only the nozzle need be disposed in the enclosure means and FIG. 6 shows this embodiment. This Figure shows holder 50 having an enclosure means 51 and upstanding panel 52. The enclosure means has a plurality of sealing apertures 53 (six being shown), in upper wall 54 of enclosure means 51. Sealing apertures 53 are of a size to snuggly fit around the uppermost portion of nozzle 3. Thus, essentially only the entire nozzle of the syringe is disposed within the enclosure means, by virtue of the size of the enclosure means and the size of sealing aperture 53.

However, in this embodiment the holder has a support means 55 disposed vertically above the upper wall 54 of the enclosure means 51 for supporting the barrel of a syringe. The support means preferably is a horizontally disposed support member projecting from upstanding panel 52 and having a plurality of support apertures 56 therein for receiving the barrel of the syringe. Preferably the support apertures have a plurality of support bendable flaps 57 disposed around the periphery 58 of each support aperture and extending radially into the support aperture so that when the support flaps 57 lie in the plane of the support member, the support member is essentially closed (in a manner quite similar to that shown at A of FIG. 5) but when the support aperture has a syringe barrel received therein, the support flaps are bent downwardly from the support member, as shown at aperture D of FIG. 6, which again is quite similar to aperture C in FIG. 5. Thus, this arrangement forms a close fit around the syringe barrel and holds the syringe barrel snuggly in the upright position so that the nozzle is not inadvertently dislodged from apertures 53 of enclosure means 51.

Preferably, in connection with all of the sealing flaps and support flaps the material of construction is such that the flaps are sufficiently bendable that a syringe or nozzle may be repeatedly received by and removed from either the sealing apertures or the support apertures and that a non-dust seal is repeatedly restablished in connection with the sealing apertures and a close fit around the syringe barrel is repeatedly restablished in connection with the support apertures. The choice of material will depend, primarily, on the number of times the syringe is received and removed from the flaps. For example, when a multi-dose syringe having four doses therein is contained in the package, this syringe will, normally, be received in and removed from the flaps no more than four times. Under these circumstances, the bendable nature of the material of construction is not critical and ordinary stiffened cardboard will be satisfactory, although it is preferred that the cardboard have a resinous finish to provide more resiliency thereto. On the other hand, if the multi-dose syringe will have many more doses therein, the material of construction should be heavily plastic coated cardboard or plastic per se. Polypropylene, polyethylene, polyvinylchloride and the like, are suitable for these applications.

While not shown in the drawings, it is preferred that a plurality of disposable caps 11 and nozzles 3 be provided in the package for serially injecting a portion of the contents of the syringe into a cow, capping the syringe and repeating the same a plurality of times until the syringe is emptied. For this purpose, conveniently, the nozzles and caps are contained in sterile, blister, or capsuled packs, preferably attached together via a tear strip or tear section so that a single nozzle and/or cap may be removed from a strip thereof and the sterile package opened for use of the nozzle and/or cap.

The best mode of the invention is where the syringe holds four doses, the package contains disposable nozzles, and the holder means is constructed of cardboard or coated cardboard and contains three to six syringes. The plastic film is heat-sealed Saran film, although polyethylene, polypropylene, polyvinyl chloride and the like heat-sealable films may be used. Further, the embodiment of FIGS. 3 through 5 is considered the best mode, since it simplifies manufacture of the holder and provides added protection for non-dust contamination of the syringe barrel. Again, the best contemplated mode includes a facsimile labeling on the outside of the enclosure means, as shown in FIG. 3, which eliminates the need for a transparent front wall.

With this best contemplated mode, the entire holder may be made by conventional cardboard stamping and folding operations, which are well known to the art and need not be described herein. The plastic film may be heat-sealed directly to the folded cardboard holder, particularly when the cardboard used has a heat-sealable coating for increasing the resiliency of the material, as explained above. This method of manufacture is most economical and produces a package which adds very little to the cost of the syringes per se and, thus, fulfills a major feature of the invention.

It is further preferred that a tear-line be provided in film 29, such as that shown at 31 of FIGS. 3 and 4. The tear-line may be a tear strip or heat-weakened line.

When the latter is provided by hot pressing the heat sealable plastic film 29, the film will seal to the enclosure 22 and upon tearing at 31, the upper portion of film 29 may be removed for access to the syringes while having intact the lower portion of film 29. The intact lower portion serves to further protect the syringes from contamination.

Tear-lines may also be used to separate multiple packages of holders. Thus, the holder of FIG. 3 may be placed in a back-to-back relation with an identical holder and overwrapped with a sealable plastic film whereby six syringes are provided in a single package. A tear-line in the overwrap will allow separation thereof with the two biostable packages.

What is claimed is:

1. A biostable, self-contained package of a plurality of veterinary syringes of the type having a cylindrical barrel, piston therein and discharge nozzle comprising:
   (a) a self-supporting and free-standing syringe holder including,
      (1) an enclosure means having upper, lower, side and end walls for receiving and completely enclosing a portion of the syringe such that at least the nozzle thereof is disposed within the enclosure means,
      (2) a plurality of circular sealing apertures in the upper wall of the enclosure means for receiving the syringes into the enclosure means,
      (3) a plurality of angularly shaped bendable sealing flaps disposed around the periphery of each sealing aperture and extending radially into the sealing aperture so that when the sealing flaps lie in the plane of the upper wall the sealing aperture is essentially closed but when the sealing aperture has a syringe received therein, the sealing flaps are bent into the enclosure means and form a close non-dust seal around the syringe wherein the sealing flaps are sufficiently bendable and resilient that a syringe may be repeatedly received by and removed from the sealing aperture and the non-dust seal is repeatedly reestablished;
   (b) a plurality of syringes received by the sealing apertures and partially disposed in and enclosed by the enclosure means, with the syringes being oriented upwardly in the vertical direction;
   (c) an upstanding panel, including support means for said syringes projecting from the enclosure means and extending vertically beyond the upwardmost portion of the syringes; and
   (d) a rupturable impervious plastic film extending from the end walls and at least one side wall of the enclosure means to a portion of the upstanding panel which is vertically beyond the syringes;
whereby the enclosure means and the syringes are biostably sealed from ambient contamination by the rupturable film and wherein when the rupturable film is removed the portion of the syringes disposed in the enclosure means is non-dust sealed from solid contamination.

2. The package of claim 1 wherein essentially the entire barrel and the nozzle of the syringe are disposed within the enclosure means.

3. The package of claim 1 wherein essentially only the entire nozzle of the syringe is disposed within the enclosure means.

4. The package of claim 3 wherein the support means is disposed vertically above the upper wall of the enclosure means for supporting the barrel of the syringe.

5. The package of claim 4 wherein the support means is a horizontally disposed support member projecting from the upstanding panel and having a plurality of support apertures therein for receiving the barrel of the syringe.

6. The package of claim 5 wherein the support apertures have a plurality of bendable support flaps disposed around the periphery of each support aperture and extending radially into the support aperture so that when the support flaps lie in the plane of the support member the support aperture is essentially closed but when the support aperture has the syringe barrel received therein, the support flaps are bent downwardly from the support member and form a close fit around the syringe barrel.

7. The package of claim 1 wherein the upstanding panel has a hanging aperture from which the package may be suspended.

8. The package of claim 7 wherein the hanging aperture is not within the rupturable film.

9. The package of claim 1 wherein a plurality of disposable caps and/or nozzles are provided in the package for serially injecting a portion of the content of the syringe into cow teats, capping the syringe and repeating the same a plurality of times until the syringe is emptied.

10. The package of claim 1 wherein the package is constructed of cardboard with a heat-sealable coating thereon and the plastic film is heat-sealed directly to the cardboard.

* * * * *